United States Patent
Frigoli et al.

(10) Patent No.: US 10,035,776 B2
(45) Date of Patent: Jul. 31, 2018

(54) PROCESS FOR THE PREPARATION OF ENZALUTAMIDE

(71) Applicant: Olon S.P.A., Rodano (MI) (IT)

(72) Inventors: Samuele Frigoli, Rodano (MI) (IT); Davide Longoni, Rodano (MI) (IT); Marco Alpegiani, Rodano (MI) (IT); Claudio Fuganti, Rodano (MI) (IT); Stefano Serra, Rodano (MI) (IT)

(73) Assignee: Olon S.P.A., Rodano (MI) (IT)

( * ) Notice: Subject to any disclaimer, the term of this patent is extended or adjusted under 35 U.S.C. 154(b) by 0 days.

(21) Appl. No.: 15/576,296

(22) PCT Filed: May 24, 2016

(86) PCT No.: PCT/EP2016/061690
§ 371 (c)(1),
(2) Date: Nov. 22, 2017

(87) PCT Pub. No.: WO2016/188997
PCT Pub. Date: Dec. 1, 2016

(65) Prior Publication Data
US 2018/0141914 A1 May 24, 2018

(30) Foreign Application Priority Data

May 28, 2015 (IT) .................. 102015000019015

(51) Int. Cl.
*C07D 233/86* (2006.01)
(52) U.S. Cl.
CPC .................. *C07D 233/86* (2013.01)
(58) Field of Classification Search
None
See application file for complete search history.

(56) References Cited

FOREIGN PATENT DOCUMENTS

| WO | 2006124118 A1 | 11/2006 |
|----|---------------|---------|
| WO | 2011106570 A1 | 9/2011  |

OTHER PUBLICATIONS

Search Report and Written Opinion of PCT/EP2016/061690 dated Sep. 16, 2016.

*Primary Examiner* — Kamal Saeed
(74) *Attorney, Agent, or Firm* — Silvia Salvadori, P.C.; Silvia Salvadori

(57) ABSTRACT

Disclosed is a process for the preparation of Enzalutamide comprising the reaction (Scheme 2), wherein R can be alkyl, aryl, aryl-alkyl or heterocyclyl.

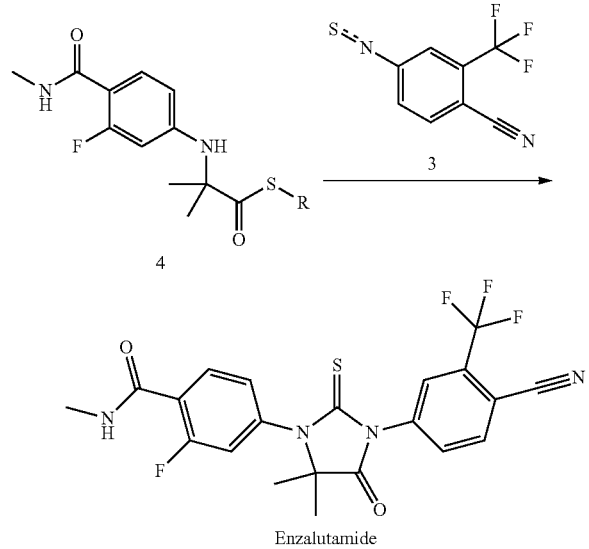

5 Claims, No Drawings

PROCESS FOR THE PREPARATION OF ENZALUTAMIDE

This application is a U.S. national stage of PCT/EP2016/061690 filed on 24 May 2016, which claims priority to and the benefit of Italian Application No. 102015000019015 filed on 28 May 2015, the contents of which are incorporated herein by reference in their entireties.

OBJECT OF THE INVENTION

The object of the invention is a process for the preparation of the active ingredient Enzalutamide.

PRIOR ART

Enzalutamide, the chemical name of which is 4-{3-[4-cyano-3-(trifluoromethyl)phenyl]-5,5-dimethyl-1-oxo-2-thioxoimidazolidin-1-yl}-2-fluoro-N-methylbenzamide,

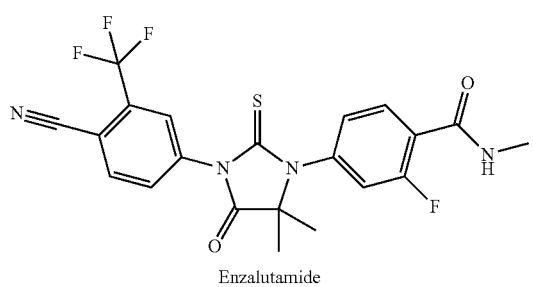 [SMILES: CNC(=O)c1ccc(N2C(=S)N(c3ccc(C#N)c(C(F)(F)F)c3)C(=O)C2(C)C)cc1F]

Enzalutamide belongs to a class of compounds able to bind to the receptors of the androgen hormones used in the treatment of metastatic prostate cancer. It is known that the antiandrogen drugs used in the treatment of hormone-sensitive prostate tumours can trigger resistance due to a mechanism of over-expression of the androgen hormone receptors, thus making the drugs ineffective, and in some cases actually counterproductive. Molecules like Enzalutamide have demonstrated their ability to make forms of tumours which have become resistant treatable again.

WO2006124118 and WO2007127010 describe a method for the preparation of Enzalutamide (Scheme 1), the last step of which is microwave-assisted cycloaddition of isothiocyanate 3 with cyanoalkylamine derivative 1. The reaction takes place with low yields, and chromatographic purification is required; moreover, the preparation of 1 requires the use of cyanides or cyanohydrin. A more efficient process for the preparation of Enzalutamide, disclosed in WO2011106570, involves cyclisation of isothiocyanate 3 with ester 2, or a superior homologue thereof (Scheme 1).

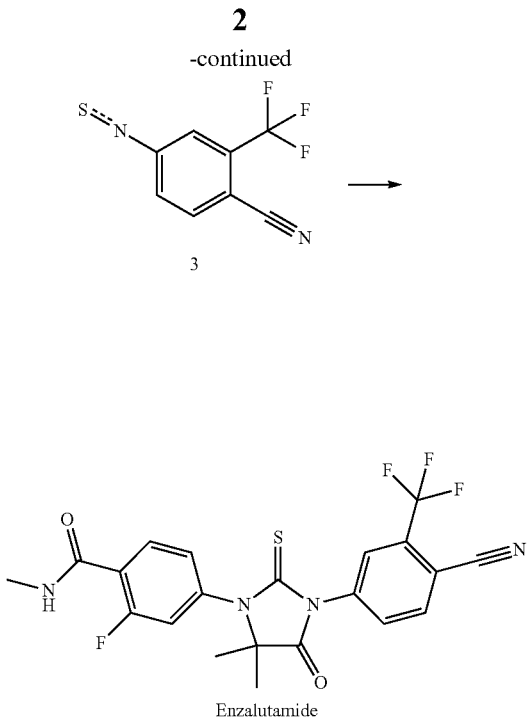

We have now found that Enzalutamide can be advantageously obtained by reacting isothiocyanate 3 with a thioester of formula 4.

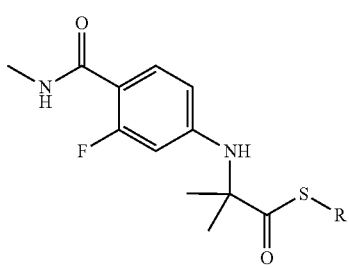

DESCRIPTION OF THE INVENTION

The object of the present invention is a process for the preparation of Enzalutamide which comprises reacting isothiocyanate 3 with a thioester of formula 5 (Scheme 2), Scheme 1

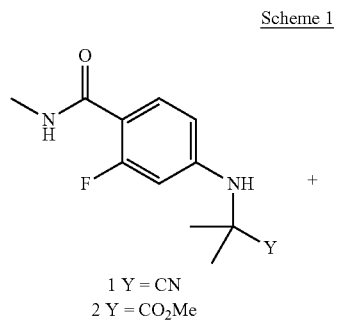

1 Y = CN
2 Y = CO$_2$Me

Scheme 2

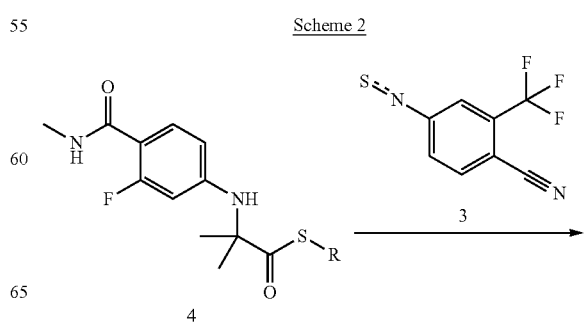

-continued

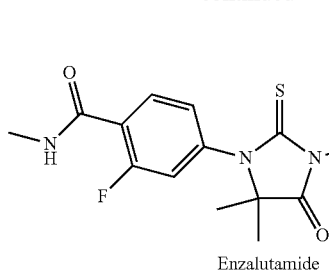

Enzalutamide wherein R can be alkyl, aryl, aryl-alkyl or heterocyclyl.

The alkyl is preferably straight or branched (C1-C10)-alkyl.

The aryl is preferably phenyl or naphthyl.

The aryl-alkyl is preferably a (C1-C4)-alkyl residue substituted by an aryl group.

The heterocyclyl is preferably a group consisting of a five or six atom ring, saturated or unsaturated, containing one or more heteroatoms selected from oxygen, sulphur and nitrogen, optionally fused to a benzene ring.

Said alkyl, aryl and heterocyclic groups can be non-substituted or substituted by one or more groups comprising: halogen, cyano, nitro, halogen, (C1-C3)-alkyl, (C3-C6)-cycloalkyl, trifluoromethyl, methoxy, methylthio, methane-sulphonyl, vinyl, allyl, carbomethoxy and carbethoxy.

The condensation between isothiocyanate 3 and a compound of formula 4 to give Enzalutamide is typically effected in an organic solvent or a mixture of solvents, selected from an ester such as propyl acetate, isopropyl acetate or butyl acetate, an amide such as N,N-dimethylformamide, N,N-dimethylacetamide or N-methyl pyrrolidone, a carboxylic acid such as acetic acid or propionic acid, an aromatic hydrocarbon such as toluene or xylene, a urea such as 1,3-dimethyl-2-imidazolidinone or N,N'-dimethyl-propylene urea, or a sulphur-containing solvent such as dimethylsulphoxide or sulfolane.

The reaction temperature typically ranges from +50° C. to +150° C., preferably from +70 to +120° C.; the reaction time ranges from 5 hours to 50 hours, preferably from 10 hours to 30 hours.

The molar ratio of compound 4 to isothiocyanate 3 usually ranges from 1:1 to 1:4, preferably from 1:1.5 to 1:2.5.

The reaction is usually effected under conditions of high concentration, with a reagent weight to solvent volume ratio preferably ranging from 1:1 to 1:4.

Enzulatamide can then be isolated by one of the classic methods, such as precipitation of the crude product by adding an anti-solvent to the reaction mixture; or dilution with a suitable solvent, optional washing of the organic solution with aqueous solutions, and obtaining the crude product by concentrating the organic phase.

The quality of the crude product can then be improved by treatment with solvent (slurry) or by crystallisation.

The compounds of formula 4 can be prepared by known methods from known products, for example by subjecting 2-(3-fluoro-4-methylcarbamoyl-phenylamino)-2-methyl-propionic acid 5 to the thioesterification reaction with an R—SH thiol of formula 6, or with an R—S—S—R disulphide of formula 7 (Scheme 4), wherein R is defined as for the compounds of formula 4.

Scheme 3

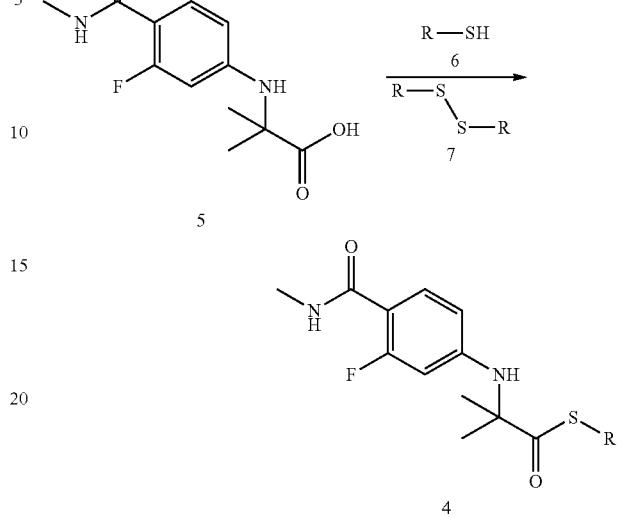

Isothiocyanate 3 and acid 5 are known products.

The invention will now be illustrated by the following examples.

Example 1

Synthesis of 2-(3-fluoro-4-methylcarbamoyl-phenylamino)-2-methyl-thiopropionic acid S-benzothiazol-2-yl ester A solution of triethylamine (0.5 ml) in dichloromethane (12 ml) is added at room temperature to a mixture of 2-(3-fluoro-4-methylcarbamoyl-phenylamino)-2-methyl-propionic acid (10 g), 2-mercaptobenzothiazolyl disulphide (15.7 g) and triethylphosphite (8.20 g) in dichloromethane (50 ml), and stirred for 4 hours. The suspension is filtered, and the organic phase is washed several times with water and a 4% sodium bicarbonate aqueous solution. The mixture is then filtered through silica, washing with DCM/AcOEt. The filtrate is evaporated to obtain 15 g of mercaptobenzothiazolyl thioester.

Example 2

Synthesis of 2-(3-fluoro-4-methylcarbamoyl-phenylamino)-2-methyl-thiopropionic acid S-phenyl ester A solution of 2-(3-fluoro-4-methylcarbamoyl-phenylamino)-2-methyl-propionic acid (5 g) and N-methyl morpholine (2 g) in anhydrous THF (60 ml) at about 0° C. is treated in sequence with isobutyl chloroformate (2.7 g), N-methyl morpholine (2 g) and thiophenol (2.2 g); the mixture is then left under stirring for 15 hours at 20° C. The mixture is diluted with ethyl acetate (100 ml), and the organic phase is washed with water, dilute hydrochloric acid, and finally with a sodium chloride saturated solution. The organic phase is concentrated, and the residue is crystallised from toluene to obtain 6 g of phenyl thioester.

Example 3

Synthesis of 2-(3-fluoro-4-methylcarbamoyl-phenylamino)-2-methyl-thiopropionic acid S-benzyl ester N,N'-Dicyclohexyl carbodiimide (5 g) and a catalytic amount of 4-dimethylaminopyridine (40 mg) are added to a solution of 2-(3-fluoro-4-methylcarbamoyl-phenylamino)-2-methyl-propionic acid (5 g) and benzyl mercaptan (5 g) in dichloromethane (40 ml). The mixture is left under stirring for 15 hours at room temperature and then filtered, washed with water, sodium bicarbonate aqueous solution, dilute hydrochloric acid, and finally with a sodium chloride saturated solution. The solvent is removed, and 6.3 g of benzyl thioester is obtained.

Example 4

By operating as described in Example 3, the following thioesters were prepared:
2-(3-fluoro-4-methylcarbamoyl-phenylamino)-2-methyl-thiopropionic acid S-ethyl ester
2-(3-fluoro-4-methylcarbamoyl-phenylamino)-2-methyl-thiopropionic acid S-isopropyl ester
1-(3-fluoro-4-methylcarbamoyl-phenylamino)-1-methyl-ethylsulphanyl]-acetic acid methyl ester
2-fluoro-4-[1-(4-methoxy-benzylsulphanyl)-1-methyl-ethylamino]-N-methyl-benzamide

Example 5

Synthesis of Enzalutamide: General Procedure

A mixture of 2-(3-fluoro-4-methylcarbamoyl-phenylamino)-2-methyl-thiopropionic acid thioester (10 mmol) and 4-isothiocyanato-2-trifluoromethyl-benzonitrile (15 mmol) in DMSO/isopropyl acetate 2:1 (5 ml) is heated at about 90° C. for 24 hours. The reaction is then cooled, diluted with isopropyl acetate and washed with water, dilute hydrochloric acid, aqueous sodium bicarbonate and brine. Crude Enzalutamide is obtained by concentrating the organic phase, and then recrystallised from isopropyl acetate/n-heptane or purified by chromatography.

The yields obtained using the thioesters described in Examples 1-4 range from 45 to 90%.

The invention claimed is:
1. A process for the preparation of 4-{3-[4-cyano-3-(trifluoromethyl)phenyl]-5,5-dimethyl-1-oxo-2-thioxoimidazolidin-1-yl}-2-fluoro-N-methylbenzamide (Enzalutamide) comprising the reaction of isothiocyanate 3 with a thioester of formula 4,

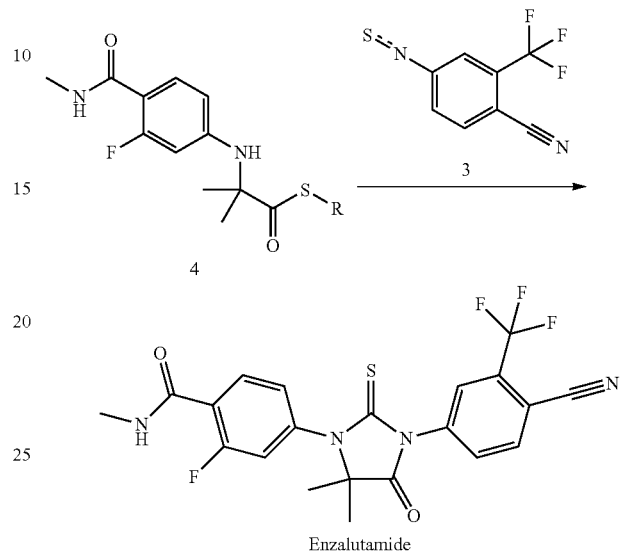

Enzalutamide wherein R can be alkyl, aryl, aryl-alkyl or heterocyclyl.

2. The process of claim 1 wherein the reaction isothiocyanate 3 and thioester 4 is carried out in a solvent selected from an ester, an amide, a carboxylic acid, an aromatic hydrocarbon, a urea or a sulphur-containing solvent and a mixture thereof.

3. The process of claim 2 wherein the solvent is selected from propyl acetate, isopropyl acetate, butyl acetate, N,N-dimethylformamide, N,N-dimethylacetamide, N-methyl pyrrolidone, acetic acid, propionic acid, toluene, xylene, 1,3-dimethyl-2-imidazolidinone, N,N'-dimethyl-propylene urea, dimethylsulphoxide, sulfolane and a mixture thereof.

4. The process according to claim 1 wherein the reaction temperature ranges from +50° C. to +150° C., and the reaction time from 5 hours to 50 hours.

5. The process according to claim 1, wherein the molar ratio of compound 4 to compound 3 ranges from 1:1 to 1:4, preferably from 1:1.5 to 1:2.5.

* * * * *